US00PP25934P3

(12) United States Plant Patent
Hill

(10) Patent No.: US PP25,934 P3
(45) Date of Patent: Sep. 22, 2015

(54) *VRIESEA* PLANT NAMED 'V858-2'

(50) Latin Name: *Vriesea* hybrid
Varietal Denomination: V858-2

(71) Applicant: Herb Hill, Lithia, FL (US)

(72) Inventor: Herb Hill, Lithia, FL (US)

(73) Assignee: 3B Funduss B.U. (NL)

( * ) Notice: Subject to any disclaimer, the term of this patent is extended or adjusted under 35 U.S.C. 154(b) by 159 days.

(21) Appl. No.: 13/998,402

(22) Filed: Oct. 28, 2013

(65) Prior Publication Data

US 2015/0121590 P1 Apr. 30, 2015

(51) Int. Cl.
*A01H 5/02* (2006.01)

(52) U.S. Cl.
USPC ..... Plt./370

(58) Field of Classification Search
USPC ..... Plt./370
See application file for complete search history.

*Primary Examiner* — Anne Grunberg
(74) *Attorney, Agent, or Firm* — Cassandra Bright

(57) ABSTRACT

A new and distinct *Vriesea* cultivar named 'V858-2' is disclosed, characterized by well-branched flaming orange-red inflorescence color. The new variety is a *Vriesea,* typically produced as an indoor ornamental plant.

1 Drawing Sheet

Latin name of the genus and species: *Vriesea* hybrid.
Variety denomination: 'V858-2'.

BACKGROUND OF THE INVENTION

This application relates to a new cultivar of *Vriesea.* The new variety is the product of a planned breeding program. The new variety originated as a seedling from the crossing of the unpatented, proprietary seed parent *Vriesea* 'v.478-1' with the unpatented, proprietary pollen parent referred to as *Vriesea* 'v.668-3'. The crossing was made by the inventor in his research greenhouse in Lithia, Fla. in October of 2003.

The new variety was first selected by the inventor, Herb Hill, a citizen of United States, in April of 2006 in a research greenhouse belonging to the inventor in Lithia, Fla. After identifying the new variety as a potentially interesting selection, the inventor continued confidential testing and propagation of 'V858-2', assessing stability of the unique characteristics of this variety.

Asexual reproduction of the new cultivar 'V858-2' was first performed at a commercial laboratory in Kudelstaart, Netherlands by tissue culture in 2008. Access to all plants was restricted, as plants were kept in a greenhouse not open to the public. Through subsequent propagation, multiple generations have been reproduced, which have shown that the unique features of this cultivar are stable and reproduced true to type.

SUMMARY OF THE INVENTION

The cultivar 'V858-2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'V858-2.' These characteristics in combination distinguish 'V858-2' as a new and distinct *Vriesea* cultivar:

1. Flaming orange-red inflorescence.
2. Green leaves.
3. Well branched inflorescence.

PARENT COMPARISON

Plants of the new cultivar 'V858-2' are similar to the seed parent in most horticultural characteristics. However the new variety, 'V858-2' differs from the seed parent in the following characteristics:

1. Shorter inflorescence.

Plants of the new cultivar 'V858-2' are similar to the pollen parent in most horticultural characteristics. However the new variety, 'V858-2' differs from the pollen parent in the following characteristics:

1. Different colored inflorescence.

COMMERCIAL COMPARISON

'V858-2' is similar in most horticultural characteristics to the patented commercial variety *Vriesea* 'Energy' U.S. Plant Pat. No. 18,235 in most horticultural characteristics. However the new variety, 'V858-2' differs from 'Energy' in the following characteristics:

1. Inflorescence of 'V858-2' branches heavier than 'Energy'.
2. Color pattern of inflorescence is flamed in 'V858-2' whereas 'Energy' is plain.

BRIEF DESCRIPTION OF THE PHOTOGRAPH

The accompanying photograph in FIG. 1 illustrates in full color a typical plant of 'V858-2' grown in a commercial greenhouse in De Kwakel, Netherlands.

The plant is 20 months old from a rooted cutting, in a 12 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a typical plant of 'V858-2' grown in a commercial greenhouse in De Kwakel, Netherlands. The plant is 20 months old from a rooted cutting, in a 12 cm pot. Temperatures ranged between 20° C. and 28° C. during the day 18° C. and 22° C. at night. No photoperiodic or chemical treatments were given to the plants. No supplemental lighting was given. Measurements and numerical values represent averages of typical plant types.

Botanical classification: *Vriesea* hybrid 'V858-2'.

PROPAGATION

Type of propagation typically used: Tissue culture.

Time to initiate roots: About 15 days at approximately 20° C.

Time to produce a rooted cutting/liner: About 180 days at approximately 22° C.

Root description: Densely branched, non-fibrous, non-fleshy, colored Greyed-orange; near RHS 165A.

PLANT

Growth habit: Main rosette with inflorescence growing from the centre; overall plant-shape: broad ovate.

Height: Approximately: 38.0 cm.

Plant spread: Approximately: 41.5 cm.

Normal pot size: 12 cm circular pot.

Growth rate: Moderate.

Branching characteristics: No stems, no lateral branches present, plant consists of a basal rosette.

Number of leaves per stem: Approximate number of leaves per rosette (no stems present): 27.

FOLIAGE

Leaf:

*Arrangement.*—Rosulate (in a basal rosette).

*Average length.*—Approximately 26.0 cm.

*Average width.*—Approximately 4.0 cm (measured at 50% of the leaf blade).

*Shape of blade.*—Ligulate.

*Aspect.*—Leaves in an average angle of 60° to horizontal (=0°).

*Apex.*—Abruptly acute, moderately to strongly twisted, tip slightly to moderately downward in an average angle of −80° to horizontal (=0°).

*Base.*—Sheathing. Sheath length: Average 7.4 cm. Sheath width: Average 7.4 cm. Sheath color: Upper side purple; in between near RHS N77C and N79B, underside purple; in between near RHS N77C and N79A.

*Margin.*—Entire.

*Texture of top surface.*—Smooth, very glossy.

*Texture of bottom surface.*—Smooth, very glossy.

*Color.*—Young foliage upper side: Green; near RHS N137A. Young foliage under side: Yellow-green; in between near RHS 146A and 147B. Mature foliage upper side: Green to yellow-green; in between near RHS N137A and 147A but much darker. Mature foliage under side: Green; near RHS N137B.

*Venation.*—Type: Parallel. Venation coloration: As leaf blade.

*Petiole.*—No petiole present.

INFLORESCENCE

General description: Scape growing from the centre of the basal rosette, inflorescence branched into a paniculate shape; only bracts visible, individual flowers not visible but fully enclosed by bracts.

*Inflorescence height, excluding scape.*—Approximately 25.9 cm.

*Inflorescence width.*—Approximately 8.8 cm.

Scape:

*Length.*—Approximately 29.3 cm.

*Width.*—Approximately 0.8 cm.

*Aspect.*—Approximately 90° angle to rosette (=0°).

*Strength.*—Strong.

*Color.*—Red; near RHS 51A.

Bracts:

*Scape/lowermost bracts.*—Shape: Ovate. Length: Approximately 2.7 cm, excluding sheath. Width: Approximately 1.8 cm (measured at the base, just above the sheath). Quantity: Average 13. Tip: Abruptly acute. Base: Sheath length: Approximately 3.0 cm. Sheath width: Approximately 2.8 cm. Sheath color: Red; near RHS 53D. Margin: Entire. Color Upper side: Lower bracts yellow-green; near RHS 146A and 146B. apex greyed-purple; near N186C, upper bracts red; near 46A, apex yellow-green; near RHS 146A. Color Under side: Lower bracts green; near RHS 143A, apex greyed-purple; near 187C, upper bracts red; near RHS 47A, tinged yellow-green, near RHS 146C, apex yellow-green; near RHS 146A.

*Terminal bracts.*—Shape: Ovate, folded (flattened). Length: Approximately 2.3 cm, excluding sheath. Width: Approximately 2.8 cm; however, bracts are folded, so in effect it is two times 1.4 cm. Quantity: Average 120. Tip: Apiculate. Base: Sheathing. Sheath length: Approximately 2.3 cm. Sheath width: Approximately 3.0 cm; however, bracts are folded, so in effect it is two times 1.5 cm. Sheath color: Orange-red; near RHS N30A. Margin: Entire. Coloration Terminal Bracts: Upper side: Orange; near RHS 24B, fading yellow-orange towards the margins; near RHS 14C. Under side: Orange-red; near RHS 34A, fading yellow-orange towards the margins; near RHS 21B.

FLOWER

Flowering characteristics: Individual flowers fully enclosed by the bracts and therefore not visible from outside.; each bract encloses one individual flower.

Days to flowering from tissue culture: 2 to 2.5 years.

Inflorescence and flower type and habit: Inflorescence paniculate, individual flower single.

Flower longevity on plant: Average: 3 months.

Quantity of buds and flowers per plant: Average: 120.

Persistent or self-cleaning: Persistent.

Bud:

*Shape.*—Lanceolate.

*Length.*—Average: 1.7 cm.

*Diameter.*—Average: 0.4 cm.

*Color.*—Yellow-green; near RHS 150B to 150C.

Flower size:
*Diameter.*—Average: 0.6 cm.
*Depth.*—Average: 2.7 cm.
Petals:
*Quantity.*—Average: 3.
*Arrangement.*—Rotate, fused.
*Length.*—Average: 1.7 cm.
*Width.*—Average: 0.5 cm.
*Shape.*—Oblong.
*Apex.*—Obtuse.
*Base.*—Broad cuneate, fused.
*Margin.*—Entire.
*Texture, upper and lower surfaces.*—Glabrous, moderately glossy.
*Color.*—When opening, upper surface: Yellow; near RHS 4C, apex yellow-green; near RHS 150A. When opening, lower surface: Yellow; near RHS 4A, 4B and 4C, tip yellow-green; near RHS N144A. Fully opened, upper surface: Yellow; near RHS 4C, apex yellow-green; near RHS 150A. Fully opened, lower surface: Yellow; near RHS 4A, 4B and 4C, tip yellow-green; near RHS N144A.
Sepals:
*Quantity.*—Average: 3.
*Length.*—Average: 2.5 cm.
*Width.*—Average: 0.9 cm.
*Shape* (*overall*).—Lanceolate. Apex: Acute. Base: Cuneate, fused.
*Margin.*—Entire.
*Color.*—Yellow; near RHS 10B, apex near RHS 8A.
Peduncles:
*Length.*—Average: 6.2 cm.
*Diameter.*—Average diameter: 0.5 cm.
*Angle.*—About 25° to the lateral branch.
*Strength.*—Strong.
*Texture.*—Glabrous, glossy.
*Color.*—Yellow-green; near RHS 150C.
Fragrance: No fragrance.

REPRODUCTIVE ORGANS

Stamen:
*Number.*—Average: 6.
Anthers:
*Shape.*—Narrow oblong.
*Length.*—Approximately 0.7 cm.
*Color.*—Yellow and yellow-orange; near RHS 13A and 12B.
*Pollen.*—No pollen detected.
Pistil:
*Number.*—Average: 1.
*Length.*—Average: 0.7 cm.
*Style.*—Length: Average: 0.65 cm. Color: Yellow-green; near RHS 150D, top darker; near RHS 151B.
*Stigma.*—Shape: Club-shaped. Color: Yellow-green; near RHS 150B. Ovary Color: Yellow-green; near RHS 150D.

OTHER CHARACTERISTICS

Disease resistance: Neither resistance nor susceptibility to the normal diseases and pests of *Vriesea* has been observed.
Temperature tolerance: Observed to tolerate temperatures to 35° C. without any negative effects. Temperature tolerance above this range has not been observed. Tolerance of cold temperatures has not been observed.
Fruit/seed production: No fruits/seeds detected to date.

What is claimed is:

1. A new and distinct cultivar of *Vriesea* plant named 'V858-2' as herein illustrated and described.

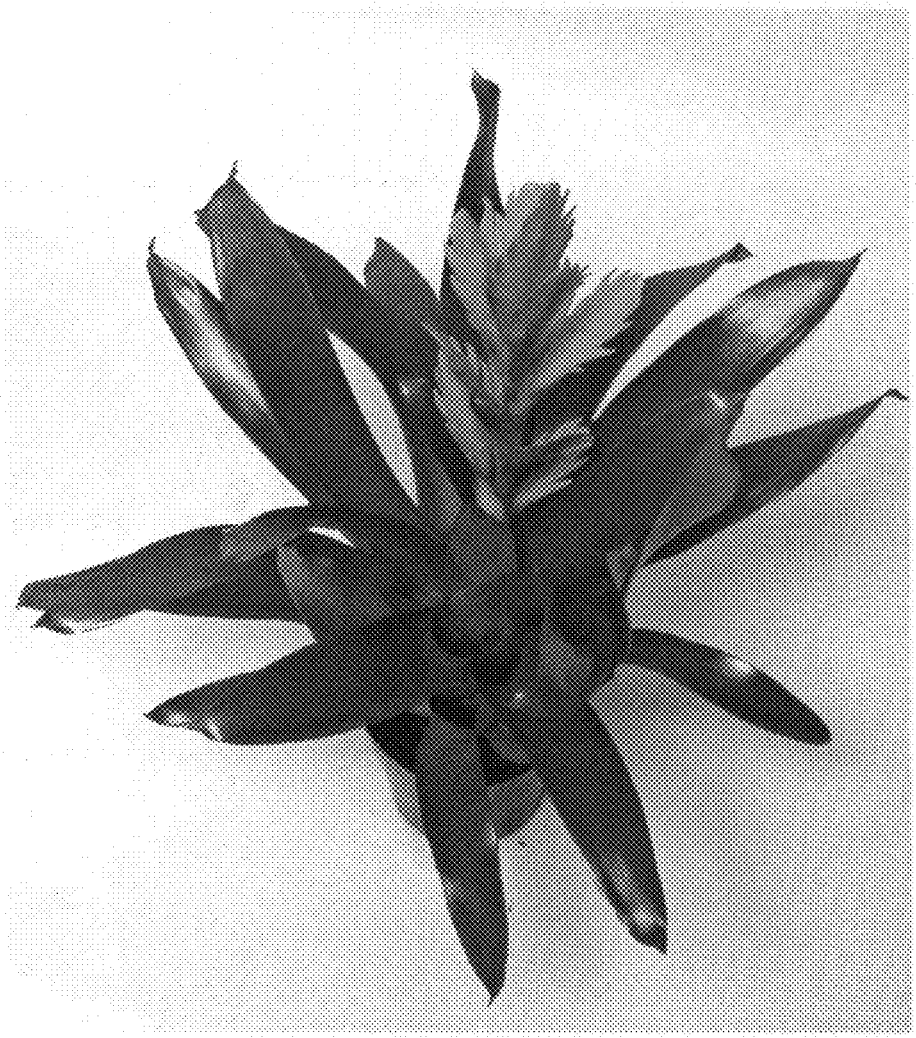

* * * * *